United States Patent
Treado et al.

(10) Patent No.: US 7,561,264 B2
(45) Date of Patent: Jul. 14, 2009

(54) SYSTEM AND METHOD FOR THE COINCIDENT DEPOSITION, DETECTION AND IDENTIFICATION OF THREAT AGENTS

(75) Inventors: Patrick J. Treado, Pittsburgh, PA (US); Charles W. Gardner, Jr., Gibsonia, PA (US); John S. Maier, Pittsburgh, PA (US)

(73) Assignee: ChemImage Corporation, Pittsburgh, PA (US)

( * ) Notice: Subject to any disclaimer, the term of this patent is extended or adjusted under 35 U.S.C. 154(b) by 170 days.

(21) Appl. No.: 11/351,286

(22) Filed: Feb. 9, 2006

(65) Prior Publication Data

US 2009/0147242 A1    Jun. 11, 2009

Related U.S. Application Data

(60) Provisional application No. 60/651,375, filed on Feb. 9, 2005.

(51) Int. Cl.
*G01J 3/44* (2006.01)
(52) U.S. Cl. ............................. 356/301
(58) Field of Classification Search ............ 356/73, 356/301
See application file for complete search history.

(56) References Cited

U.S. PATENT DOCUMENTS

| 4,880,052 | A |   | 11/1989 | Meyer, IV et al. |
|---|---|---|---|---|
| 4,884,886 | A | * | 12/1989 | Salzman et al. ............ 356/367 |
| 5,194,912 | A |   | 3/1993  | Batchelder et al. |
| 5,241,179 | A | * | 8/1993  | Carrieri ................. 250/341.6 |
| 5,377,004 | A |   | 12/1994 | Owen et al. |
| 5,442,438 | A |   | 8/1995  | Batchelder et al. |
| 5,528,393 | A |   | 6/1996  | Sharp et al. |
| 5,539,517 | A |   | 7/1996  | Cabib et al. |
| 5,623,342 | A |   | 4/1997  | Baldwin et al. |
| 5,689,333 | A |   | 11/1997 | Batchelder et al. |
| 5,710,626 | A |   | 1/1998  | O'Rourke et al. |
| 5,862,273 | A |   | 1/1999  | Pelletier |
| 5,866,430 | A |   | 2/1999  | Grow |
| 5,901,261 | A |   | 5/1999  | Wach |
| 5,911,017 | A |   | 6/1999  | Wach et al. |
| 5,982,484 | A |   | 11/1999 | Clarke et al. |
| 6,002,476 | A |   | 12/1999 | Treado |
| RE36,529  | E |   | 1/2000  | Lewis et al. |

(Continued)

FOREIGN PATENT DOCUMENTS

JP    9-121889 A    5/1997

(Continued)

OTHER PUBLICATIONS

Caetano et al., "Evaluation of the Importance of Non-Linear Spectral Mixing in Coniferous Forests," SPIE vol. 3499, Sep. 1998, pp. 257-269.

(Continued)

*Primary Examiner*—Kara E Geisel
*Assistant Examiner*—Abdullahi Nur
(74) *Attorney, Agent, or Firm*—Morgan Lewis & Bockius LLP (57) ABSTRACT

A system and method for depositing a sample of a threat agent is deposited onto a substrate. The threat agent is identified substantially coincident in time with the depositing of the sample of the threat agent onto the substrate.

15 Claims, 6 Drawing Sheets

U.S. PATENT DOCUMENTS

| | | | | |
|---|---|---|---|---|
| 6,040,191 | A * | 3/2000 | Grow | 436/172 |
| 6,614,532 | B1 * | 9/2003 | Power et al. | 356/432 |
| 6,717,668 | B2 | 4/2004 | Treado et al. | |
| 6,734,962 | B2 | 5/2004 | Treado et al. | |
| 6,765,668 | B2 | 7/2004 | Gardner et al. | |
| 6,806,465 | B2 * | 10/2004 | Anderson et al. | 250/287 |
| 6,917,423 | B2 | 7/2005 | Gardner et al. | |
| 6,954,667 | B2 | 10/2005 | Treado et al. | |
| 6,965,793 | B2 | 11/2005 | Treado et al. | |
| 6,985,818 | B1 * | 1/2006 | Samuels | 702/22 |
| 7,268,868 | B2 * | 9/2007 | Kiesel et al. | 356/301 |
| 2005/0162647 | A1 * | 7/2005 | Okumura et al. | 356/316 |

FOREIGN PATENT DOCUMENTS

WO PCT/US2006/004561  8/2007

OTHER PUBLICATIONS

Rasmussen et al., "Library Retrieval of Infrared Spectra Based on Detailed Intensity Information," Applied Spectroscopy, vol. 33, No. 4, Feb. 1979, pp. 371-376.

Guilment et al., "Infrared Chemical Micro-Imaging Assisted by Interactive Self-Modeling Multivariate Analysis," Applied Spectroscopy, vol. 48, No. 3, 1994, pp. 320-326.

Malinowski, Edmund R., "Factor Analysis in Chemistry," 1991, 2nd Edition, published by John Wiley & Sons, Inc. / William H. Press et al., pp. 32-82 and pp. 208-265.

* cited by examiner

FOCAL PLANE DISPERSION AXIS -λ

SPATIAL INFORMATION

SYSTEM AND METHOD FOR THE COINCIDENT DEPOSITION, DETECTION AND IDENTIFICATION OF THREAT AGENTS

RELATED APPLICATIONS

This application claims the benefit of U.S. Patent Application No. 60/651,375 filed Feb. 9, 2005 entitled Development of a Biological Raman Electrostatic Detector Identifier (BioREDI) Sensor.

FIELD OF DISCLOSURE

This application relates generally to systems and methods for detecting and identifying hazardous agents.

BACKGROUND

Deployment of threat agents poses significant threats to both human and economic heath. This threat is compounded by a limited ability to detect deployment of the agents. Prior art detection strategies rely on separate instrumentation for detection and identification of the threat agent. Conventional means of detecting airborne matter include relatively non-specific optical and spectroscopic methods, including laser scattering, ultraviolet laser induced fluorescence (UV-LIF) and laser induced breakdown spectroscopy (LIBS). Conventional means to identify a threat agent include wet chemical methods or spectroscopic methods. Reagent-based identification of biological threat agents includes methods such as specific antibodies, genetic markers and propagation in culture. While highly specific, these identification methods are time-consuming, labor-intensive and costly. Spectroscopic means, for identification, provide an alternative to reagent-based identification methods and include mass spectrometry, infrared spectroscopy, Raman spectroscopy, and imaging spectrometry. Mass spectrometry is limited by sensitivity to background interference. Infrared spectroscopy exhibits low sensitivity. Raman spectroscopy can be implemented in several different configurations, including normal Raman spectroscopy, UV resonance Raman spectroscopy, surface enhanced Raman spectroscopy (SERS) and non-linear Raman spectroscopy. While normal Raman spectroscopy has demonstrated adequate sensitivity and specificity for detection of airborne matter, other forms of Raman spectroscopy suffer from inadequate sensitivity, specificity or signature robustness. Prior art imaging spectroscopy is limited by the need to switch from a broad band light source, for optical imaging, to a substantially monochromatic light source for spectroscopic imaging. This results in a signification time period between detection and identification during which time the sample may degrade.

The present disclosure describes a reagent free sensor using Raman spectroscopy and Raman imaging spectroscopy to detect and identify a sample simultaneous with sample deposition. The system and methods of the present disclosure may operate in either a trigger mode or an identification mode. The present disclosure describes an approach that reduces system and method complexity by using a single illumination source.

SUMMARY

The present disclosure provides a system and method for depositing a sample of a threat agent onto a substrate. The threat agent is detected and identified substantially coincident in time with the deposition of the sample of the threat agent onto the substrate. Optionally, a fiber array spectral translator that converts a non-linear field of view of a portion of the substrate containing the sample to a curvilinear map coupled to an entrance slit of a spectrometer is used to collect spatially-resolved Raman spectra suitable for identifying the threat agent.

In one embodiment, the threat agent deposited on the substrate is illuminated, via a single illumination source, with a plurality of photons to thereby produce elastic scattered photons and Raman scattered photons. Identifying the threat agent may be performed by analyzing the elastic scattered photons, produced by the threat agent on the substrate, using elastic scattering imaging to form an image of the threat agent, and analyzing the Raman scattered photons, produced by the threat agent on the substrate, using Raman spectroscopy. A Raman spectrum may be compared to at least one reference Raman library spectrum to identify the threat agent. Analysis of the Raman scattered photons may further include generating Raman spectra anywhere within the Raman shift range of about 0 $cm^{-1}$ to about 3500 $cm^{-1}$ at a spectral resolution less than 20 $cm^{-1}$. Analysis of the Raman scattered photons may further include generating multiple spatially independent image channels simultaneously within a Raman shift of about 0 $cm^{-1}$ to about 3500 $cm^{-1}$ at a full spectral resolution less than 20 $cm^{-1}$.

In one embodiment, analysis of the elastic scattered photons produced by the threat agent includes automatically focusing the image of the threat agent on the substrate using one of the following: a CMOS detector, a CCD detector or a high frame rate digital detector, in combination with a feedback control mechanism. Analysis of the Raman scattered photons also may include passing the Raman scattered photons through a device selected from the group consisting of a tunable filter, a band pass filter, a liquid crystal tunable filter, an interferometer, an acousto optic tunable filter and a dispersive optical device, to produce the plurality of spatially resolved Raman spectra. Analysis of the Raman scattered photons may also include passing the Raman scattered photons through one of the following: a line scan spectrometer; a multi-point spectrometer; a single point spectrometer; and area imaging spectrometer spectrometer.

In one embodiment, the elastic scattered photons and the Raman scattered photons are collected using an optical system, wherein said illumination source is located along an optical path, and said substrate is located along a plane wherein the optical path or the deposition apparatus is at an angle other than 90° with respect to the substrate plane.

In one embodiment, the system and method for depositing and identifying the threat agent operates in a trigger mode that detects a presence or absence of the threat agent, and an identification mode that identifies the threat agent. The trigger mode may use a trigger time period and the identification mode may use an identification time period, and wherein the trigger time period is less than the identification time period. In one embodiment, the identification mode is initiated upon detecting the presence of the threat agent in the trigger mode. An additional amount of the threat agent may be accumulated during operation in the identification mode. In one embodiment, the identification mode may be initiated substantially simultaneous upon detecting the present of the threat agent in the trigger mode.

Depositing the threat agent onto the substrate may be accomplished using ultrasonic deposition, electro spray and inertial impaction of the threat agent onto the substrate. In one embodiment, depositing the sample of the threat agent onto the substrate includes depositing at least 50 particles onto the substrate. Depositing the sample of the threat agent onto the substrate may include collecting air from a confined environment or an outside environment.

The threat agent may be hazardous agent comprising a bacterium, virus, protozoan, biological toxin, fungus, a chemical agent, a radiological material and an explosive material and/or may be an airborne particulate matter or aerosol matter.

In accordance with a further aspect, the present disclosure provides a system and method for depositing a sample of a threat agent onto a substrate. A single illumination source illuminates the threat agent deposited on the substrate with a plurality of photons to thereby produce elastic scattered photons and Raman scattered photons. The threat agent on the substrate is identified. The system and method operate in a trigger mode that detects the presence or absence of the threat agent, and an identification mode that identifies the threat agent. Optionally, a fiber array spectral translator that converts a non-linear field of view of a portion of the substrate containing the sample to a curvilinear map coupled to an entrance slit of a spectrometer which is used for identifying the threat agent.

Deposition of the sample of the threat agent onto the substrate may occur prior to identification of the threat agent on the substrate. A background level of the substrate may be identified before deposition of the sample of the threat agent onto the substrate. In this embodiment, identifying the threat agent on the substrate occurs substantially coincident in time with or after the depositing of the sample of the threat agent onto the substrate.

In accordance with a further aspect, the present disclosure provides a system and method for depositing a sample of a threat agent onto a substrate. The deposition of the threat agent onto the substrate is visually observed by analyzing the elastic scattered photons produced by the threat agent using elastic scatter imaging to form an image of the threat agent on the substrate, wherein depositing of the threat agent is substantially coincident in time with visually observing of the deposition of the threat agent. Analyzing the elastic scattered photons produced by the threat agent may include automatically focusing the image of the threat agent on the substrate using a CMOS detector, a CCD detector or a high frame rate digital detector, in combination with a feedback control mechanism. The elastic scattered photons may be collected via an optical system, wherein the optical system is positioned relative to the substrate and moved relative to the position of the substrate to focus the image of the threat agent on the substrate. Image contrast in the image of the threat agent on the substrate may be improved by removing an interference pattern of the illumination source via mode scrambling and frame averaging. Visually observing deposition of the threat agent onto the substrate is performed without a spectrometer.

In accordance with a still further aspect, the present disclosure provides a system and method for depositing a sample of a threat agent onto a substrate. A single illumination source illuminates the threat agent on the substrate with a plurality of photons to thereby produce elastic scattered photons. Deposition of the threat agent onto the substrate is visually observed by analyzing the elastic scattered photons produced by the threat agent using elastic scatter imaging to form an image of the threat agent on the substrate.

In accordance with a still further aspect, the present disclosure provides a system and method for identifying a sample of a threat agent that is deposited onto a substrate. A first optical collection device collects at least one of the following: elastic scattered light produced by the threat agent, and Raman scattered light produced by the threat agent. A second optical collection device collects Raman scattered light produced by the threat agent, wherein the second optical collection device comprises a two dimensional non-linear array of optical fibers drawn into a one dimensional fiber stack that converts a non-linear field of view into a curvilinear map, wherein the curvilinear fiber stack is coupled to an entrance slit of a Raman spectrometer. The threat agent deposited on the substrate is identified using Raman spectroscopy.

In accordance with yet a further aspect, the present disclosure provides a system and method for identifying a sample of a threat agent that is deposited onto a substrate. The threat agent is illuminated via an illumination source with a plurality of photons to thereby produce photons transmitted, reflected, emitted or Raman scattered by the threat agent. An optical system collects elastic scatter photons produced by the threat agent and at least one of photons transmitted, reflected, emitted or Raman scattered by the threat agent, wherein said illumination source is located along an optical path, and said substrate is located along a plane wherein the optical path or the deposition apparatus is at an angle other than 90° with respect to the substrate plane. The depth of field of the optical system is extended by passing at least one of the following through a phase mask: elastic scattered photons, and photons transmitted, reflected, emitted or Raman scattered by the threat agent.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure.

In the drawings.

DESCRIPTION OF THE EMBODIMENTS

Reference will now be made in detail to the embodiments of the present disclosure, examples of which are illustrated in the accompanying drawings. Wherever possible, the same reference numbers will be used throughout the drawings to refer to the same or like parts.

Figure 1:
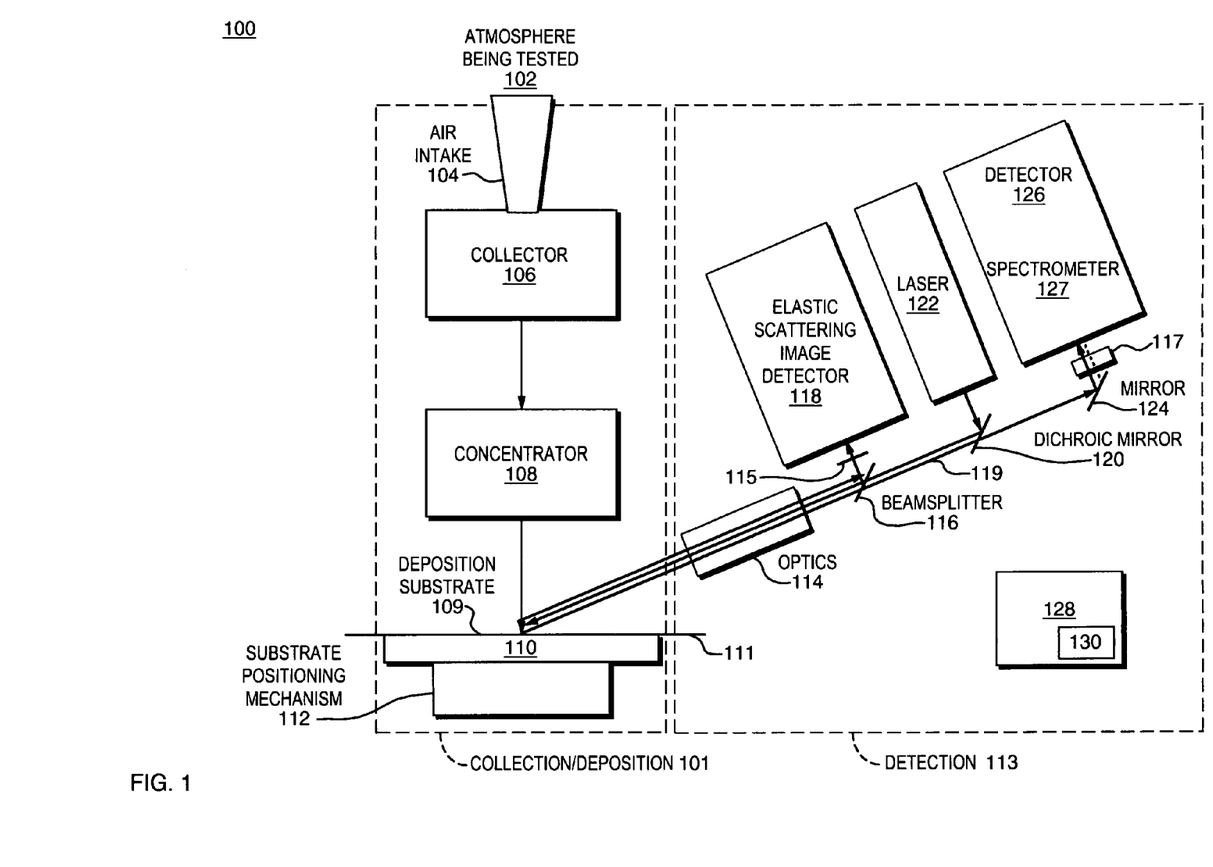
FIG. 1 illustrates a system used in connection with the present disclosure.

FIG. 1 illustrates system 100 which may be used to carry out the methods of the present disclosure. System 100 includes a deposition means 101 and a detector means 113. The deposition means may include an air intake port 104, which is open to the surrounding environment 102, a collector 106, a concentrator 108, a sample 109, a deposition substrate 110 (e.g., a compact disc), substrate plane 111 and a substrate positioning mechanism 112. The identification means 113 comprises a first optical system 114, an optional phase mask 115, a beam splitter 116, a second optical system 117, an optical path 119, an elastic scattering image detector 118, an illumination source 122, a dichroic mirror 120, a mirror 124, a spectroscopic detector 126, spectrometer 127 and a processor 128 having a spectral library 130.

As illustrated in FIG. 1, the sample is collected from the surrounding environment 102 and then concentrated. The sample may comprise airborne particulate matter or aerosol matter. The surrounding environment 102 includes a confined environment and an outside environment. The confined environment includes a building, storage container, plane, train or other mass transportation vehicle and a human respiratory system. To collect air from a confined environment, system 100 is connected to the air conditioning or heating system of a building, vehicle or storage container that circulates air to the confined environment.

The sample collected and identified by system 100 includes a threat agent. The threat agent comprises a hazardous agent and includes a bacterium, virus, protozoan, biological toxin, fungus, a chemical agent, a radiological material and an explosive material. The bacterium includes Anthrax, Bacillus, Streptococcus, Staphylococcus, *Escherichia*, *Erwinia*, and *Pseudomonas*. The virus includes a pathogenic virus selected from smallpox, influenza and E. bola viruses. The biological toxin includes ricin. The hazardous substance is any substance that may cause disease, injury, discomfort, pain, or death to an animal such as a human.

The sample may be collected and concentrated using a variety of devices. In one embodiment, the sample is collected using an aerosol collector in combination with a virtual impactor which eliminates air and concentrates the sample. In second embodiment, the sample is collected using an aerosol collector in combination with a liquid concentrator. This collection and concentration process takes place on the order of a fraction of a second to minutes depending on the velocity of the collecting air. The concentrated sample is subsequently deposited onto the surface of the substrate. The sample may be deposited onto the surface of the substrate using inertial impaction, ultrasonic deposition, and electro spray deposition.

In one embodiment, ultrasonic deposition is used to deposit the sample onto the substrate. In one embodiment, a wet walled cyclone collector may be used to collect aerosol and particulate matter. The analyte-containing fluid, which can be connected to a reservoir, including a water storage tank, can be used to provide analyte-containing fluid to the ultrasonic nozzle liquid inlet port. The ultrasonic nozzle may also contain a compressed air inlet to focus the deposition of the liquid input onto the substrate surface. The ultrasonic spray device may be used to perform a plurality of spray applications over the same spatial location to increase the analyte concentration in a desired field of view. In one embodiment, ultrasonic spray devices such those manufactured by Sono-Tek Corporation of Milton, N.Y. may be used for implementing the present disclosure.

The deposition device deposits a plurality of sample particles 109 onto the substrate 110. In one embodiment, at least 1 sample particle is deposited onto the substrate. In another embodiment, at least 50 sample particles are deposited onto the substrate. In another embodiment, at least about 50-250 sample particles are deposited onto the substrate. In another embodiment, at least about 250-2500 sample particles are deposited onto the substrate. In another embodiment, at least about 2500-10,000 sample particles are deposited onto the substrate. In another embodiment, at least about 10,000-100,000 sample particles are deposited onto the substrate. In another embodiment, at least about 100,000-1,000,000 sample particles are deposited onto the substrate.

With further reference to FIG. 1, system 100 uses a single illumination source 122, directed along an optical path 119, to illuminate the sample with a plurality of photons to thereby produce elastic scattered photons and photons transmitted, reflected, emitted or Raman scattered by the sample. In one embodiment, the illumination source illuminates the sample with a plurality of photons to produce elastic scattered photons and Raman scattered photons. The illumination source includes a low power laser. Low power lasers manufactured by Coherent Inc, Santa Clara, Calif. or the Spectra-Physics Division of Newport Inc., Mountain View, Calif. are suitable. In one embodiment, the optical path 119 of the illumination source 122 is at an angle other than 90° from the plane 111 defined by the two dimensional substrate 110. In another embodiment the deposition means 101 is at an angle other than 90° from the plane 111 defined by the two dimensional substrate 110.

With further reference to FIG. 1, system 100 has a first optical system 114. In one embodiment, the optical system 114, collects elastic scattered photons, produced by the sample. In a second embodiment, the optical system 114, collects elastic scattered photons and Raman scattered photons produced by the sample. In a third embodiment, the optical system 114, collects elastic scattered photons, and at least one of photons transmitted, reflected, emitted or Raman scattered produced by the sample.

With further reference to FIG. 1, system 100 may include a phase mask 115. The phase mask 115 will be used to extend the depth of field of the optic system by passing through the phase mask 115 at least one of elastic scattered photons and photons transmitted, reflected, emitted or Raman scattered produced by the sample.

Figure 2A:
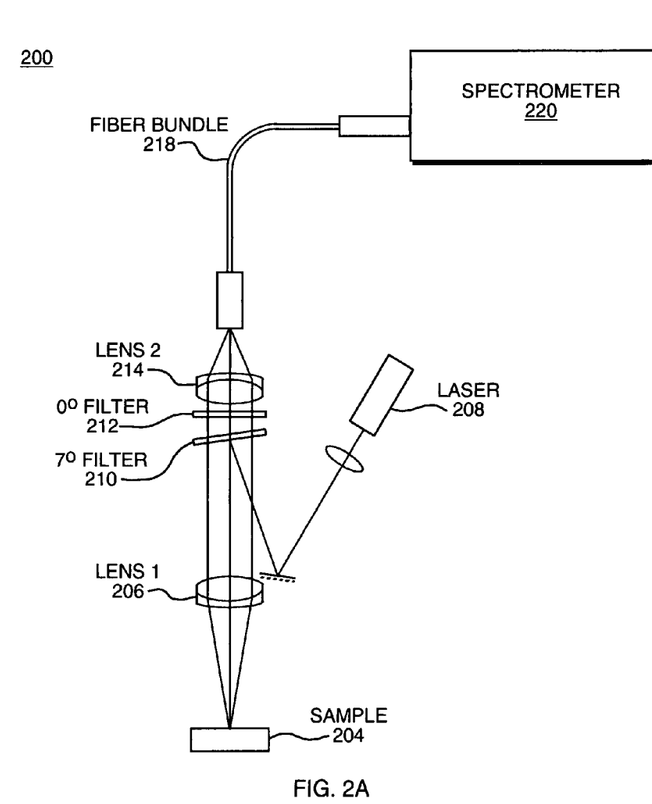
FIG. 2 illustrates a device used in the system of this disclosure.
Figure 2B:
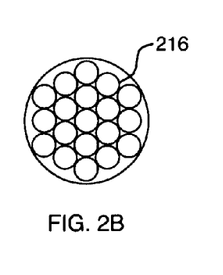

One embodiment of the system 100 may include a second optical system, a fiber array spectral translator ("FAST"). With reference to FIG. 2, the FAST system 200 includes a first lens 206, an illumination source 208, a first filter 210, a second filter 212 a second lens 214, a first end of a fiber bundle 216 and a second end of the fiber bundle 218 which is connected to a spectrometer 220. The first lens 206 acts as a collecting lens which focuses the illumination source onto the sample 204 and collects all photons, other than elastic scattered photons, at wavelengths other than laser wavelength; this includes photons emitted or Raman scattered by the sample. Photons transmitted or reflected by the sample will have the same wavelength as the laser and will be blocked by filter element 212. Lens 206 collimates the photons produced by the sample projecting the photons into infinity. The second lens 214 is used in combination with the first lens 206 to form images at the final focal plane of the second lens 214. The first end of the fiber bundle 216 is comprised of a two dimensional non-linear array of fiber bundles. The second end of the fiber bundle 218 is comprised of a curvilinear array of fiber bundles wherein curvilinear may include a straight line as well as a curved line configurations.

In one embodiment of the present disclosure, system 100 utilizes an elastic scatter imaging detector 118 to visually observe deposition and form an image of the sample on the substrate by analyzing elastic scattered photons produced by the sample. The image is used to assess sample deposition density, morphology and focusing. In one embodiment, the elastic scatter imaging, to visually observe deposition, is used in the absence of an imaging spectrometer. In a second embodiment, system 100 employs an elastic scatter imaging detector 118 in combination with a spectrometer 127 for identification of the sample. In one embodiment, the elastic scatter imaging detection and spectrometric identification are performed simultaneously, using a single low power illumination source for identification of the sample.

With further reference to FIG. 1, the elastic scatter imaging detector 118 is comprised of one of the following of a CMOS detector, a CCD detector and a high frame rate digital detector. The system uses the detector 118 in combination with a feedback and control mechanism to automatically focus the sample under the collection optic. In one embodiment, a light gathering objective of the optical system 114 is moved relative to the position of the substrate to focus the image of the sample on the substrate. The spectrometer 127 could employ detectors such as CCDs, CMOS, CIDs (charge injection device), diode arrays, photomultiplier tube (PMT), PMT array, avalanche photodiode.

Figure 3A:
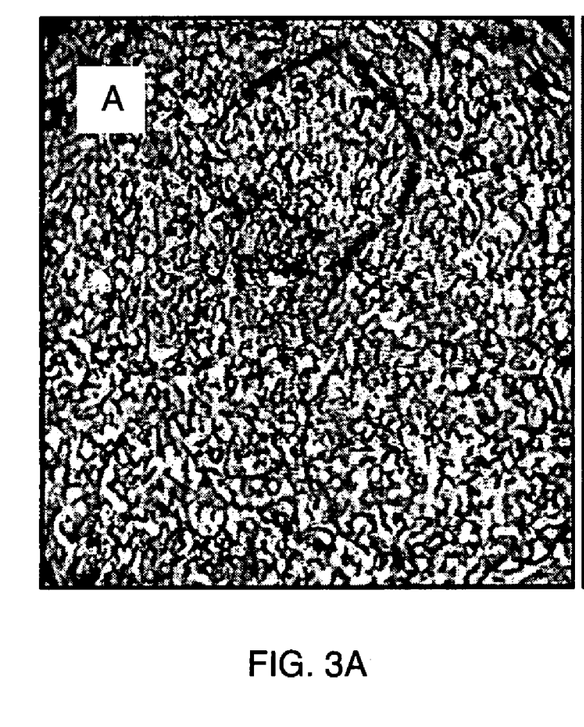
FIGS. 3A and 3B illustrate an elastic scatter image produced by the system and methods of the present disclosure.
Figure 3B:
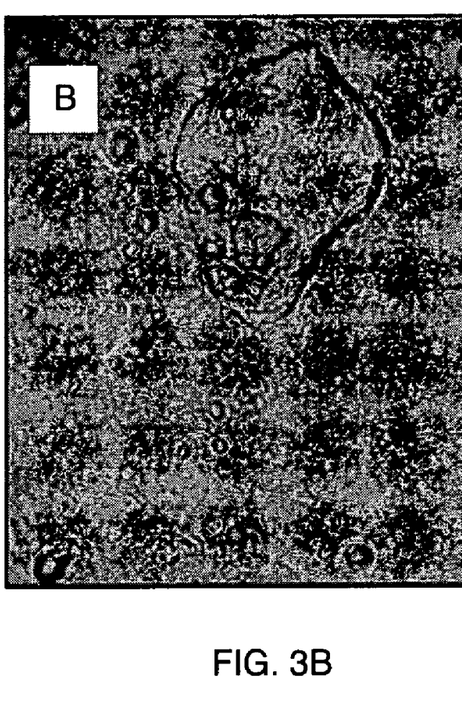

In one embodiment of the present disclosure, the elastic scatter image of the sample is collected on the detector and mode scrambling and frame averaging are used to improve the image contrast by removing the interference pattern of the illumination source producing the final image. FIGS. 3A and 3B illustrate an elastic scatter image of human epithelial cells obtained by one embodiment of the system of the present disclosure. A low power laser source illuminated the sample of human epithelial cells to generate the elastic scatter image of the sample which produces a high cross section elastic scatter image signal. However, the elastic scatter image is typically masked by the presence of a laser interference pattern. The laser interference pattern is removed by mode scrambling and frame averaging. As illustrated in FIG. 3A, the human epithelial cells are not readily observable due to the presence of a laser interference (i.e. speckle) pattern masking the presence of the inherently low contrast cellular object within the field of view of the 20× objective employed to capture the image. As illustrated in FIG. 3B, the cell is readily observable by using a fiber optic to scramble the modes traversing the fiber optic, which effectively makes the monochromatic laser light incoherent. A plurality of images is time averaged and the cellular image contrast is enhanced by effective suppression of the coherent laser speckle pattern. To obtain the image in FIG. 3B, ten images were each collected at 30 frames per second.

In another embodiment of the present disclosure, the elastic scatter image of the sample is obtained by collecting the scattered photons using an optical system, wherein the optical path 119 of the illumination source 122 or the deposition means 101 is at an angle other than 90° from the plane 111 defined by the two dimensional substrate 110. In one embodiment, this is achieved by operating the objective, which collects the elastic scattered photons, at 60° off axis from the plane of the substrate. This embodiment produces a finite rectangular region of interest in focus but this region of interest will be smaller than the objective field of view. In order to compensate for the out of focus regions of interest, extended depth of field ("EDF") optical compensation may be used to image over the full field of view of the microscope objective. To implement EDF, a phase mask will be located in the elastic scatter image collection optical path to modify the incoherent optical system in such a way that the point spread function ("PSF") is insensitive to misfocus, while forming an optical transfer function ("OTF") that has no regions of zero values within its pass band. Because the OTF has no regions of zeros, digital processing can be used to "restore" the sampled intermediate image. Further, because the OTF is less sensitive to misfocus, the same digital processing restores the image for all values of misfocus. This combined optical/digital systems produces a PSF that is comparable to that of the diffraction limited PSF, but over a far larger region of focus. Typically, an 8× increase in the DOF is achievable.

In another embodiment, system 100 utilizes a spectrometer 127 in combination with an elastic scatter imaging detector 118 to identify the sample. The elastic scattered photons, produced by the threat agent, are analyzed using elastic scatter imaging to produce an image of the sample on the substrate. In one embodiment, a spectrometer is used to analyze at least one of photons transmitted, reflected, emitted or Raman scattered by the sample, using spectroscopy. In another embodiment, a spectrometer is used to analyze at least one of photons transmitted, reflected, emitted or Raman scattered by the sample, using spectroscopic imaging to produce a plurality of spatially resolved spectra. The spectrometer may operate in one or more of the following spectral ranges: the ultraviolet (UV), visible, near infrared, and mid-infrared. The spectrometer may operate to collect images based on the following detection modalities: UV, visible, near-IR or mid-IR absorption imaging in either transmission or reflectance modes; Raman scatter imaging; fluorescence; photoluminescence; chemiluminescence; and electroluminescence imaging. The spectrometer may operate in conjunction with polarized light microscopy and/or differential interference contrast imaging. Photons transmitted, reflected, emitted or Raman scattered by the sample, are passed through a filter to produce a plurality of spatially resolved spectra. The filter may be a tunable filter, a band pass filter, a liquid crystal tunable filter, an interferometer, an acousto optic tunable filter or a dispersive optical device. The photons transmitted, reflected, emitted or Raman scattered may be passed through a spectrometer which may be a line scan spectrometer; a multi-point spectrometer; a single point scan spectrometer or area imaging spectrometer. In one embodiment, the spectrometer may be used in an imaging mode to produce a plurality of spatially resolved spectra arising from the sample volume illuminated by the illumination source. In another embodiment, the spectrometer may be used in a non-imaging mode by summing all of the spectra collected in the imaging mode to form a composite spectrum arising from the sample volume illuminated by the illumination source. In another embodiment, the spectrometer may be used in a non-imaging mode to collect a composite spectrum arising from the sample volume illuminated by the illumination source.

In one embodiment, the spectrometer includes a Raman imaging spectrometer that analyzes Raman scattered photons produced by the sample. In one embodiment, Raman imaging spectrometer generates Raman spectra anywhere within the range of Raman shift of 0-3500 $cm^{-1}$ at a full spectral resolution of less than 20 $cm^{-1}$. In one embodiment, the Raman imaging spectrometer simultaneously captures multiple spatially independent spectra, up to 1000, within the range of Raman shift of 0-3500 $cm^{-1}$ at a full spectral resolution of less than 20 $cm^{-1}$. In one embodiment, the spectrometer comprises a Raman line imaging spectrometer. In another embodiment, the spectrometer comprises a dispersive Raman line imaging spectrometer.

Figure 4A:
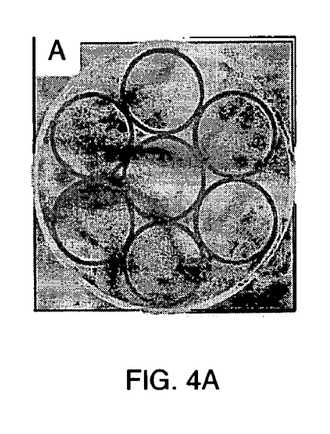
FIGS. 4A, 4B, 4C and 4D illustrate Raman imaging analysis using the system and methods of the present disclosure.
Figure 4B:
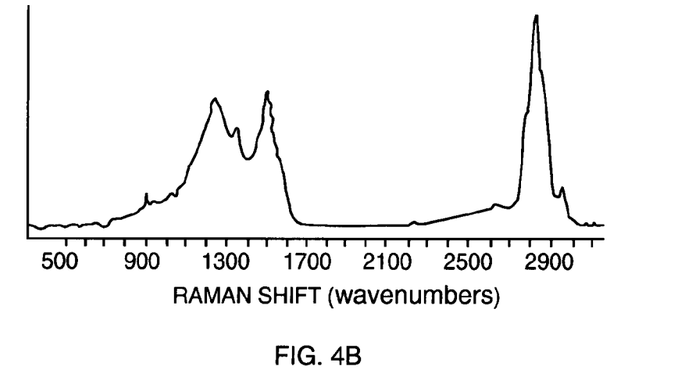
Figure 4C:
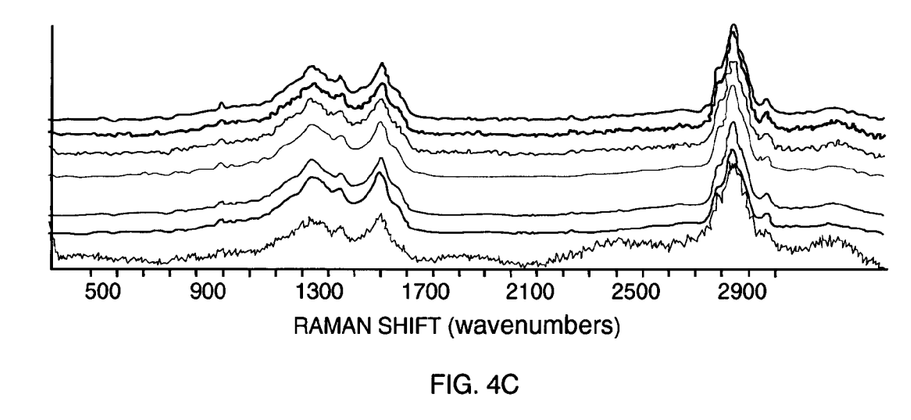
Figure 4D:
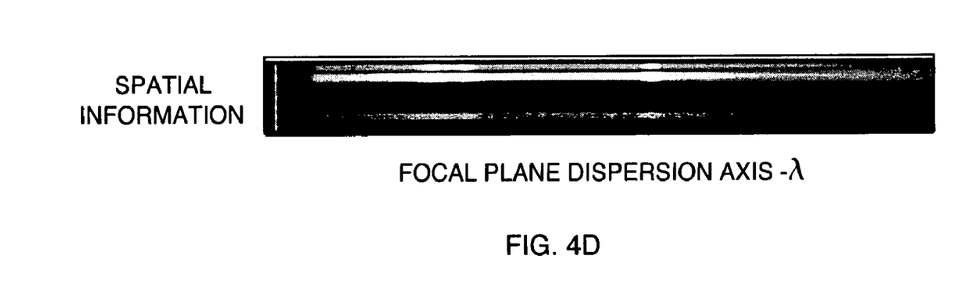

In one embodiment, the sample is identified using a spectrometer in combination with a fiber array spectral translator. With reference to FIG. 4, a plurality of Raman spectra were collected on a ChemImage FALCON II Raman microscope from a physical mixture of a sample comprised of ovalbumin ("Ova") and diesel soot ("DS") The spatially resolved Raman spectra collected from the sample were mapped to the entrance slit of the FALCON II's dispersive Raman spectrometer, using a coherent fiber optic bundle (FAST). Using FAST, a fiber the circular field of view of the image is converted to a curvilinear shape that is mapped to the entrance slit of the spectrometer. The benefits of this approach include rapid collection of the full Raman image spectral hypercube without the need for spatial or spectral scanning mechanisms. Because multiple Raman spectra can be captured within a wide field of view without the need to reposition the laser, fluorescence photo bleaching time can be minimized. In addition, the spatially resolved Raman spectra map the local heterogeneity of the sample mixture which enables target testing based spectral unmixing. As a result, sample mixtures are analyzed in real time if sufficient single to noise reduction is achieved. FIG. 4A illustrates the optical image of Ova/DS under 100× objective magnification. FIG. 4B illustrates a dispersive Raman spectrum representing the average response of the mixture sample, and FIG. 4C illustrates seven spatially resolved dispersive Raman spectra collected from the sample using FAST. FIG. 4D illustrates the dispersive Raman spectral image collected at the focal plane of the spectrometer. The seven independent spatial channels images along the y axis and the Raman spectrum along the x axis of the focal plane are clearly visible.

In yet another embodiment, system 100 will utilize a phase mask 115 to extend the depth of field of the optical system. In this embodiment, a sample 109 will be deposited onto a substrate 110. The sample will be illuminated via an illumination source 112 along an optical path 119 with a plurality of photons producing elastic scattered photons and at least one of photons transmitted, reflected, emitted or Raman scattered by the sample. The sample may comprise a threat agent. An optical system will collect the elastic scatter photons produced by the sample and at least one of photons transmitted, reflected, emitted or Raman scattered by the threat agent. The illumination source 122 will be located along the optical path 119, and said substrate 110 will be located along a plane 111 wherein the optical path 119 is at an angle other than 90° with respect to the substrate plane 111. In another embodiment, the deposition means 101 will be located at an angle other than 90° with respect to the substrate plane 111. The depth of field of the optical system will be extended by passing at least one of the following through the phase mask 115: elastic scattered photons, and photons transmitted, reflected, emitted or Raman scattered by the threat agent. The sample will be identified based at least in part on the output of the phase mask 115, by (1) analyzing the elastic scattered photons using elastic scattering imaging 118 to form an image of the sample; and (2) analyzing at least one of photons transmitted, reflected, emitted or Raman scattered by the sample using spectroscopic imaging 126 to produce a plurality of spatially resolved spectra. The photons transmitted, reflected, emitted or Raman scattered will be passed through a filter to produce a plurality of spatially resolved spectra. The sample deposition and identification will occur: substantially coincident in time with each other; deposition prior to identification; background identification followed by deposition which may be substantially coincident or prior to identification.

The method of the present disclosure provides for deposition, visual observation and identification of the sample. In one embodiment, the sample is visually observed and identified substantially coincident in time with the deposition of the sample onto the surface of the substrate. The deposition process takes place over a fraction of a second from the deposition of the first particle to the deposition of a particle density sufficient to generate a measurable signal which permits the detection and identification of the sample, via the imaging spectrometer. The system of this disclosure has demonstrated that a measurable signal, sufficient to visually observe and identify the sample via Raman imaging spectroscopy, may be observed in as short as 10 seconds after being illuminated by the illumination source. In one embodiment, the particle density, required for observation and identification, is 20 sample particles deposited on the substrate, in the detector field of view for a five minute identification mode. In another embodiment, the sufficient particle density may be as small as 1 particle of a sample deposited on the substrate. In the case of bioaerosols, the sample occurs as individual spores or cells or aggregates of cells. A single cell generates a measurable Raman signal wherein the time period for the Raman process, to generate a measurable signal, is initiated within femtoseconds after being illuminated by the illumination source. Therefore, instantaneous deposition, observation and identification of a single cell are envisioned.

System 100 is used in a method of the present disclosure provides for deposition and identification of a threat agent. In a preferred embodiment, the particle sample deposition is substantially coincident with identification of the particle sample. For the purposes of this application, the term substantially coincident means that sample deposition occurs on approximately the same time period as sample identification, ideally without the requirement that the sample substrate be re-positioned relative to the deposition apparatus, or detection apparatus during the deposition and identification processes. In one embodiment, the time between deposition of analyte on the substrate and identification is as short as 10 seconds, under conditions that the sample is illuminated continuously by the illumination source. In another embodiment, the particle sample identification occurs after sample deposition. In another embodiment, a background level measurement of the sample substrate is made followed by sample deposition which occurs substantially coincident or prior to identification of the sample.

In another embodiment, system 100 is used in a method of the present disclosure provides for deposition and visual observation of a threat agent. In a preferred embodiment, the particle sample deposition is substantially coincident with visual observation of the particle sample. For the purposes of this application, the term substantially coincident means that sample deposition occurs on approximately the same time period as sample observation, ideally without the requirement that the sample substrate be re-positioned relative to the deposition apparatus, or detection apparatus during the deposition and observation processes. In one embodiment, the time between deposition of analyte on the substrate and observation is as short as 10 seconds, under conditions that the sample is illuminated continuously by the illumination source. In another embodiment, the particle sample observation occurs after sample deposition. In another embodiment, a background level measurement of the sample substrate is made followed by sample deposition which occurs substantially coincident or prior to observation of the sample.

System 100 may operate in a trigger mode or an identification mode. The trigger mode detects the presence of a threat agent and the absence of a threat agent. The trigger mode has a trigger time period. The trigger time period may range from a fraction of a second to about 60 seconds. At high concentrations of a threat agent, the trigger time period may be substantially instantaneous. A one-minute or less trigger cycle time allows for sampling the environment dynamically to monitor the onset of threats and to manage highly variable background conditions.

The identification mode identifies the threat agent and has an identification time period. In one embodiment, the trigger time period is less than the identification time period. In another embodiment, the identification mode is initiated upon detecting the present of the threat agent in the trigger mode. In another embodiment, the identification mode is initiated substantially simultaneously upon detecting the present of the threat agent in the trigger mode. In another embodiment, an additional amount of sample is accumulated while the system is operating in the identification mode.

If the trigger mode is initiated, system 100 changes over to the confirmation mode under the system software. In the confirmation mode, collection and deposition of additional particles continues during a continuous 5 minutes interrogation of the sample by the imaging system. No movement of the sample or alignment of sample is needed; the transition from trigger to confirmation is instantaneous. During the confirmation time, all particles are examined due to the continuous collection.

System 100 also includes a processor 128 that determines the mode of operation and the identification of the sample. The processor employs different algorithm when system 100 is operation in the trigger mode or confirmation mode. In one embodiment, the algorithm includes constant false alarm rate algorithms. Other algorithms include target testing, a Bayesian approach and a matched filter approach based on Mahalanobis Distance. Approaches to sample identification are disclosed in: U.S. patent application Ser. No. 10/812,233, filed Mar. 29, 2004 entitled Method for Identifying Components of a Spectral Analysis; PCT International Appl. No. PCT/US05/013036 filed Jul. 14, 2005 entitled Method and Apparatus for Multimodal Detection; and U.S. Provisional Patent Appl. No. 60/688,812, filed Jul. 9, 2005, entitled Forensic Integrated Search Technology (FIST) each of which is incorporated herein in its entirety.

To identify the sample, the plurality of spatially resolved spectra, produced by the imaging spectrometer, are compared to at least one reference library spectrum to identify the threat agent. In one embodiment, the plurality of spatially resolved Raman spectra are compared to at least one reference Raman library spectrum to identify the threat agent.

In one embodiment, processor 128 utilizes a target testing for unmixing signatures and searching the measured mixture spectra relative to the pure component signature library in an automated fashion. Target testing based spectral unmixing compares mixture spectra against pure component library spectra by characterizing the mixture space using principal component analysis ("PCA"); ranking the library spectra by quantifying their goodness of fit into the mixture data space; and determining by target testing the number and identity of the pure spectra present in the mixture sample.

With further reference to FIG. 4, the sample was classified as diesel soot using a Euclidian Distance (ED) matched filter identifier algorithm. The ED algorithm assumes samples are pure components, which was an inaccurate assumption. When the spatially resolved dispersive Raman spectra are analyzed using a target testing spectral unmixing algorithm, the mixture sample was correctly classified as being comprised of Ova and carbonaceous material; a material class comprised of DS and humic acid, because of their Raman spectral similarity.

The target testing algorithm includes the following general steps:
1. Use PCA on the mixture spectra to characterize the mixture data space.
2. Calculate the angle of projection of each library spectrum with the mixture data space. A dot product of a vector with an n-dimensional space. A dot product of 1.0 represents a perfect fit into the data space.
3. Rank all library spectra by the angle of projection into the mixture data space.
4. Consider all permutations of the top matches as ranked by angle. Determine the n most likely candidate pure components. Generate all possible m component solutions, where m varies from 1 to n and is the number of library spectra in a given solution.
5. For each candidate solution calculate the correlation coefficient; calculate projected library spectra for each set of m component library spectra (given the known mixture spectra and the known library spectra). Calculate the correlation coefficient of each projected library spectrum with the actual library spectrum. The correlation coefficient used as the selection criterion is the square root of the sum of squares of the dot products for each member of a given m component solution.
6. The most probable solution is the one with the highest correlation coefficient.

The target testing algorithm requires a Raman signature library that supports differentiation between threat agents, near neighbors, and clutter independent of agent growth or preparation conditions and sample history. Raman spectra of threat agents include certain spectral bands that are highly sensitive to growth conditions and others that are relatively insensitive to growth conditions. The detection and identification algorithms will focus on spectral bands that maximize agent discrimination, but minimize sensitivity to growth conditions. This can minimize signature library dependence on unwanted biological contributions to variability.

With further reference to FIG. 1, system 100 includes a deposition substrate 110 and substrate positioning mechanism 112. The substrate 110 provides for the deposition of a plurality of samples at predetermined sites. The substrate 110 includes a compact disk ("CD") configuration or any similar circular or non-circular, substantially flat surface of metal or non-metal. The substrate 110 is to enable autonomous focusing of the Raman laser on the substrate. In one embodiment, the substrate includes a standard audio CD dimensions for the substrate allowing for collection of approximately 1,800 samples on a standard 120 mm diameter CD. System 100 also includes storage unit capable of holding 25 substrates to support 30 days worth of sampling, 43,800 samples collected in 30 days@1,800 samples per substrate. The concept is for the substrate-disks to be supplied in a cartridge that can be easily swapped out after 30 days of operation. The storage system includes a marking technique to log the archived samples for conditions at the point of data collection e.g., time, date, sensor settings, and for sample relocation. The substrate positioning device 112 includes a motion stage having two degrees of freedom, directional linear motion and rotationally variable. The motion of the substrate positioning device 112 generates sample deposits in spiral tracks, circular concentric tracks, or in linear tracks. The substrates are stored in a storage system designed to protect the resilience of the deposition spots to mechanical shock/vibration, humidity, and other physicochemical agents that might degrade their stability.

EXAMPLES

Figure 5:
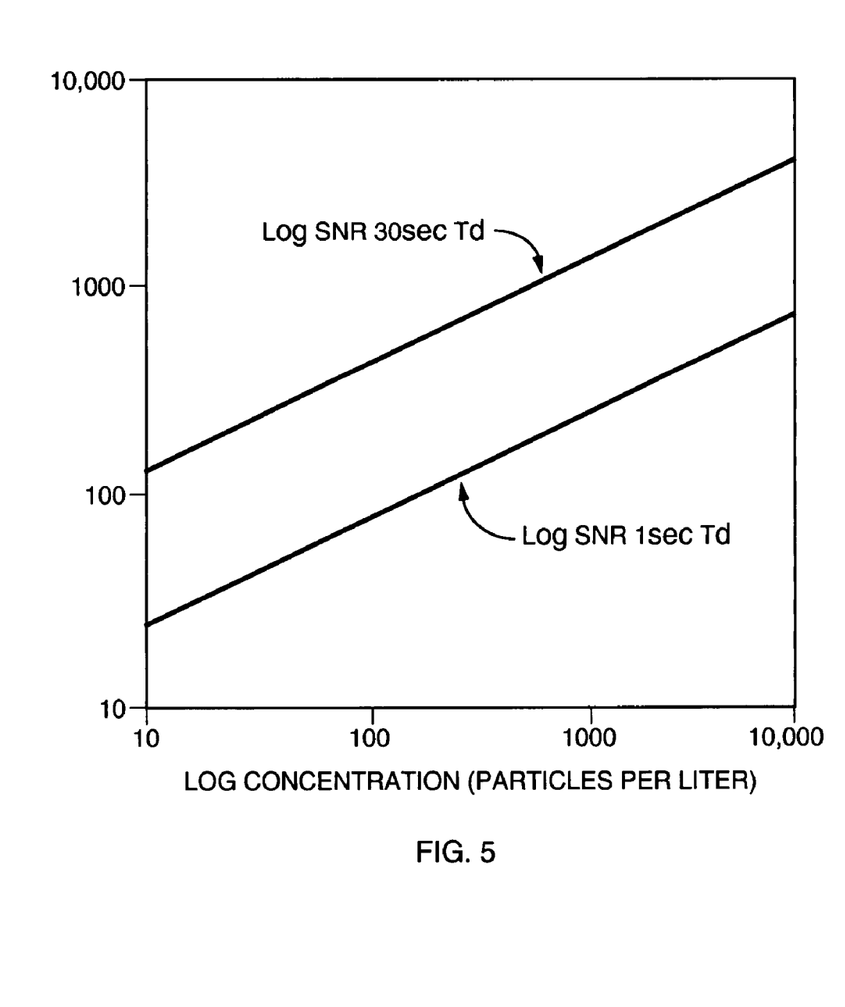
FIG. 5 illustrates the estimated sensitivity of detection and identification using the system and methods of the present disclosure.

FIG. 5 illustrates the estimated sensitivity of Raman imaging spectroscopy detection technology. The plot compares system 100 estimated signal to noise ("SNR") vs. bio-aerosol concentration for both trigger and confirmation detection modes. The estimations were made using a ChemImage Raman system performance model.

As shown in FIG. 5, increasing the time for detection ("$T_d$") results in improved SNR, which enables improved detection sensitivity. In trigger detection mode, we estimate a LOD of ~800 particles per liter (PPL) cells is achievable. In confirmation detection mode, a LOD of 100 PPL cells is achievable. LOD is defined as the minimum bio-threat concentration detectable, in a reproducible manner, at a probability of detection ("Pd") greater than 90%, at the specified $T_d$ and a defined probability of false alarm ("$P_{fa}$"). The acceptable false alarm rate is determined by operational requirements. However, we have assumed that in trigger detection mode ($T_d$-30 secs, $P_d$>90%), an acceptable level of false alarms is 5/day ($P_{fa}$-1.7×10$^3$). In confirmation mode ($T_d$-300 secs $P_d$>90%), the required $P_{fa}$ is 1/month ($P_{fa}$-1.1×10$^4$). The calibration curves shown in FIG. 5 are generated using a Raman detection SNR performance model.

The present disclosure may be embodied in other specific forms without departing from the spirit or essential attributes of the disclosure. Accordingly, reference should be made to the appended claims, rather than the foregoing specification, as indicated the scope of the disclosure. Although the foregoing description is directed to the preferred embodiments of the disclosure, it is noted that other variations and modification will be apparent to those skilled in the art, and may be made without departing from the spirit or scope of the disclosure.

What is claimed is:

1. A method comprising:
   depositing a sample of a threat agent onto a substrate;
   identifying the threat agent substantially coincident in time with the depositing of the sample of the threat agent onto the substrate;
   illuminating, via a single illumination source, the threat agent deposited on the substrate with a plurality of photons to thereby produce elastic scattered photons and Raman scattered photons; and
   wherein identifying the threat agent comprises:
      analyzing the elastic scattered photons, produced by the threat agent on the substrate, using elastic scattering imaging to form an image of the threat agent; and
      analyzing the Raman scattered photons, produced by the threat agent on the substrate, using Raman spectroscopy.

2. The method of claim 1, further comprising comparing a Raman spectrum to at least one reference Raman library spectrum to identify the threat agent.

3. The method of claim 1, wherein analyzing the Raman scattered photons further comprises generating Raman spectra anywhere within a Raman shift range of about 0 cm$^{-1}$ to about 3500 cm$^{-1}$ at a spectral resolution less than 20 cm$^{-1}$.

4. The method of claim 1, wherein analyzing the Raman scattered photons further comprises generating multiple spatially independent image channels simultaneously anywhere within a Raman shift of about 0 cm$^{-1}$ to about 3500 cm$^{-1}$ at a full spectral resolution less than 20 cm$^{-1}$.

5. The method of claim 1, wherein analyzing the elastic scattered photons produced by the threat agent comprises automatically focusing the image of the threat agent on the substrate using one of the following: a CMOS detector, a CCD detector or a high frame rate digital detector, in combination with a feedback control mechanism.

6. The method of claim 1, wherein analyzing the Raman scattered photons comprises passing said Raman scattered photons through a device selected from the group consisting of a tunable filter, a band pass filter, a liquid crystal tunable filter, an interferometer, an acousto optic tunable filter and a dispersive optical device, to produce the plurality of spatially resolved Raman spectra.

7. The method of claim 1, wherein analyzing the Raman scattered photons comprises passing the Raman scattered photons through one of the following:
   a line scan spectrometer to produce a plurality of spatially-resolved Raman spectra arising from a sample volume illuminated by the illumination source;
   a multi-point spectrometer to produce a plurality of spatially-resolved Raman spectra arising from a sample volume illuminated by the illumination source;
   a single point spectrometer to produce a plurality of spatially-resolved Raman spectra arising from a sample volume illuminated by the illumination source;
   an area imaging spectrometer to produce a plurality of spatially-resolved Raman spectra arising from a sample volume illuminated by the illumination source; and
   a point spectrometer to produce a single Raman spectrum arising from a sample volume illuminated by the illumination source.

8. The method of claim 1, further comprising collecting the elastic scattered photons and the Raman scattered photons using an optical system, wherein said illumination source is located along an optical path, and said substrate is located along a plane wherein the optical path is at an angle other than 90° with respect to the substrate plane.

9. The A method comprising:
   depositing a sample of a threat agent onto a substrate;
   identifying the threat agent substantially coincident in time with the depositing of the sample of the threat agent onto the substrate;
   illuminating, via a single illumination source, the threat agent deposited on the substrate with a plurality of photons to thereby produce elastic scattered photons and Raman scattered photons;
   operating in a trigger mode that detects one of the following:
      a presence of the threat agent,
      and absence of the threat agent; and
   operating in an identification mode that identifies the threat agent.

10. The method of claim 9, wherein said trigger mode having a time period and said identification mode having an identification time period, and wherein said trigger time period is less than the identification time period.

11. The method of claim 9, further comprising initiating the identification mode upon detecting the presence of the threat agent in the trigger mode.

12. The method of claim 9, further comprising accumulating an additional amount of the threat agent during operation in the identification mode.

13. The method of claim 9, further comprising initiating the identification mode substantially simultaneous upon detecting the presence of the threat agent in the trigger mode.

14. A method comprising:
   depositing a sample of a threat agent onto a substrate; and
   identifying the threat agent substantially coincident in time with the depositing of the sample of the threat agent onto the substrate;
   wherein identifying the threat agent comprises using a fiber array spectral translator to convert a non-linear field of view of a portion of said substrate containing the sample to a curvilinear map coupled to an entrance slit of a spectrometer; and
   wherein the spectrometer is used to collect Raman spectra suitable for identifying the threat agent.

15. A system, comprising:
   means for depositing a sample of a threat agent onto a substrate; and
   means for identifying the threat agent substantially coincident in time with the depositing of the sample of the threat agent onto the substrate by the means for depositing;
   wherein the means for identifying comprises a spectrometer and a fiber array spectral translator that converts a non-linear field of view of a portion of said substrate containing the sample to a curvilinear map coupled to an entrance slit of the spectrometer; and wherein the spectrometer is used to collect Raman spectra suitable for identifying the threat agent.

* * * * *